(12) United States Patent
Hasumi

(10) Patent No.: US 9,907,819 B2
(45) Date of Patent: *Mar. 6, 2018

(54) THERAPY AND METHODS OF INTRODUCING IMMATURE DENDRITIC CELLS AND/OR CYTOTOXIC T LYMPHOCYTE AND ANTI-TNF ANTIBODY FOR TREATMENT OF TUMORS

(71) Applicant: Hasumi International Research Foundation, Washington, DC (US)

(72) Inventor: Kenichiro Hasumi, Tokyo (JP)

(73) Assignee: Kenichiro Hasumi, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/549,706

(22) Filed: Nov. 21, 2014

(65) Prior Publication Data

US 2015/0079032 A1    Mar. 19, 2015

Related U.S. Application Data

(63) Continuation-in-part of application No. 13/928,844, filed on Jun. 27, 2013, now Pat. No. 8,961,957.

(60) Provisional application No. 61/907,053, filed on Nov. 21, 2013, provisional application No. 61/664,998, filed on Jun. 27, 2012.

(51) Int. Cl.
| | |
|---|---|
| *A01N 63/00* | (2006.01) |
| *A61K 45/00* | (2006.01) |
| *A61K 47/00* | (2006.01) |
| *A61K 35/15* | (2015.01) |
| *A61K 39/395* | (2006.01) |
| *C12N 5/0784* | (2010.01) |
| *C12N 5/0783* | (2010.01) |
| *A61K 35/17* | (2015.01) |
| *C07K 16/24* | (2006.01) |
| *A61K 38/19* | (2006.01) |
| *A61K 39/00* | (2006.01) |

(52) U.S. Cl.
CPC .............. *A61K 35/15* (2013.01); *A61K 35/17* (2013.01); *A61K 38/19* (2013.01); *A61K 39/3955* (2013.01); *A61K 39/39558* (2013.01); *C07K 16/241* (2013.01); *C12N 5/0638* (2013.01); *C12N 5/0639* (2013.01); *A61K 2039/5154* (2013.01); *C12N 2501/25* (2013.01)

(58) Field of Classification Search
None
See application file for complete search history.

(56) References Cited

U.S. PATENT DOCUMENTS

| | | | |
|---|---|---|---|
| 7,226,593 B2 * | 6/2007 | Le et al. | 424/145.1 |
| 8,088,397 B2 | 1/2012 | Hasumi et al. | |
| 2005/0123522 A1 | 6/2005 | Punnonen et al. | |
| 2006/0045881 A1 * | 3/2006 | Molldrem | A61K 39/0011 424/178.1 |
| 2008/0160050 A1 * | 7/2008 | Hasumi | 424/277.1 |
| 2009/0148452 A1 * | 6/2009 | Wakkach et al. | 424/139.1 |
| 2010/0203010 A1 | 8/2010 | Hariharan et al. | |

FOREIGN PATENT DOCUMENTS

WO    2014/004809 A2    1/2014

OTHER PUBLICATIONS

Baker eta l., 20001, Blood. vol. 97: 2923-31.*
Oyelaran, O. et al., "Evaluation of Human Antibody Responses to Keyhole Limpet Hemocyanin on a Carbohydrate Microarray"; Proteomics Clin. Appl.; 2010; pp. 285-294; vol. 4.
Hasumi, K. et al., "Therapeutic Response in Patients With Advanced Malignancies Treated With Combined Dendritic Cell—Activated T Cell Based Immunotherapy and Intensity—Modulated Radiotherapy"; Cancers; Apr. 2011 (Apr. 28, 2011); pp. 2223-2242; vol. 3.

* cited by examiner

*Primary Examiner* — Amy Juedes
(74) *Attorney, Agent, or Firm* — Eckert Seamans Cherin & Mellott, LLC; Carol A. Marmo

(57) ABSTRACT

The invention relates to therapy and methods of applying the therapy to a patient. The invention includes the introduction of immature dendritic cells into the patient and the introduction of anti-TNF antibody into the patient. The immature dendritic cells are introduced intratumorally and/or through vessel and the anti-TNF antibody is introduced intratumorally and/or through vessel and/or subcutaneously. The immature dendritic cells can be formed by collecting monocyte cells from the patient and culturing the cells in a culture medium. The invention can be effective to regress, reduce or eliminate tumor cells in tumor tissue of the patients, including metastasized tumors. Further, the treatment of the invention is effective in the absence of conventional therapy, such as radiotherapy and chemotherapy.

18 Claims, 4 Drawing Sheets

THERAPY AND METHODS OF INTRODUCING IMMATURE DENDRITIC CELLS AND/OR CYTOTOXIC T LYMPHOCYTE AND ANTI-TNF ANTIBODY FOR TREATMENT OF TUMORS

CROSS-REFERENCE TO RELATED APPLICATIONS

This application claims priority under 35 U.S.C. Section 119(e) from Provisional Application 61/907,053, entitled "Therapy and Methods of Introducing Immature Dendritic Cells and/or Cytotoxic T Lymphocyte and Anti-TNF Antibody for Treatment of Tumors" filed on Nov. 21, 2013, and this application is a Continuation-In-Part (CIP) of Nonprovisional application Ser. No. 13/928,844, which claims priority from Provisional Application 61/664,998, both entitled "Therapy and Method for Intratumorally Introducing Cytotoxic T Lymphocyte and/or NKT Cell With Anti-TNF and/or Anti-IL-10" filed on Jun. 27, 2013 and Jun. 27, 2012, respectively.

FIELD OF THE INVENTION

The invention relates to tumor cell and tumor tissue therapy, and methods for applying the therapy to treat a cancer patient. The invention includes introducing intratumorally and/or through vessel immature dendritic cells and/or cytotoxic T lymphocytes to the patient, and introducing intratumorally and/or through vessel and/or subcutaneously anti-tumor necrosis factor (anti-TNF) antibody to the patient. The tumor therapy and methods of the invention are effective to treat the patient in the presence or in the absence of conventional therapy, such as chemotherapy and/or radiotherapy.

DESCRIPTION OF THE PRIOR ART

Cytotoxic T lymphocytes (CTLs) are an important component of cellular immunity. They play a critical role in the control of many infections and cancers. These T cells are responsible for "hunting down" other cells of the body that are infected by viruses or are cancer-containing, and destroying them. For example, when a virus or cancer is using a cell to reproduce, the cell displays some of the viral proteins or cancer components on its surface. The cytotoxic T cells can recognize these proteins or components and hone-in to destroy the infected or cancer-containing cells before they can release the new infection or cancer into the bloodstream. Many vaccines are effective, at least in part, by stimulating this type of T cell activation or response. CTLs can also create chemicals known as cytokines which assist in coordinating how the immune system fights against disease.

Tumor necrosis factor (TNF) is a cytokine which circulates throughout a body. TNF is critical for effective immune surveillance and is required for proper proliferation and function of natural killer cells, T cells, e.g., CTLs, B cells, macrophages, and dendritic cells. The primary role of TNF is in the regulation of immune cells. Further, it is known in the art that TNF can cause systemic inflammation which can result in various chronic conditions. Anti-TNF antibody, also known as TNF blockers or inhibitors, interfere with the body's production of TNF.

According to published data, i.e., from the American Cancer Society, it is estimated that 1,665,540 new cancer cases will be diagnosed and 585,720 cancer deaths will occur in 2014, in the United States. Cancer remains the second most common cause of death in the United States and accounts for nearly 1 of every 4 deaths.

Known cancer treatment procedures can be expensive, time-consuming and invasive. Further, these known procedures may not be capable of regressing, reducing or eliminating cancer in certain patients.

Thus, there is a need in the art to develop new cancer therapy and methods of applying the cancer therapy to regress, reduce or eliminate tumor cells in tumor tissue of a patient. It is desirable for the therapy and methods of application to be effective in a reasonable period of time and further, desirable for the therapy and methods of application to be as minimally invasive to the patient as reasonably possible. Furthermore, it is advantageous for the therapy and methods to be effective in the absence of subjecting the patient to conventional therapy regimens, such as, radiotherapy and/or chemotherapy.

SUMMARY OF THE INVENTION

The invention solves the above need by providing effective therapy and methods for regression, reduction or elimination of tumor cells in tumor tissue of a patient, as well as tumor cells in metastasized tumors. In one aspect, the invention provides a method of introducing intratumorally and/or through vessel a therapeutically effective amount of immature dendritic cells and/or CTLs into the patient, and introducing intratumorally and/or through vessel and/or subcutaneously a therapeutically effective amount of anti-TNF antibody into the patient.

In certain embodiments, the method can further include collecting monocyte cells and/or the CTLs from a patient, culturing the monocyte cells and/or the CTLs, forming immature dendritic cells from the monocyte cells, and re-introducing the cultured immature dendritic cells and/or the cultured CTLs back into the patient. The re-introducing of the cultured CTLs can be conducted prior to or following or coincident with the introducing of the cultured immature dendritic cells.

The monocyte cells can be cultured in a medium including IL-4, GM-CFS, and mixtures thereof to form immature dendritic cells. The CTLs can be cultured in a medium including IL-2, CD3, and mixtures thereof.

In certain embodiments, the introducing of the anti-TNF antibody can be coincident with the introducing of the immature dendritic cells and/or CTLs. In other embodiments, the introducing of the anti-TNF antibody can be immediately following or following a short time thereafter the introducing of the immature dendritic cells and/or CTLs. A short period of time can include seconds or minutes or hours or days. In general, the anti-TNF antibody is introduced when there is a sufficient amount of CTLs present in the auto-immune system of the patient, such that the immune response of the CTLs is supported by suppressing the activity of the TNF.

The introducing of the immature dendritic cells and/or CTLs, and/or the introducing of the anti-TNF antibody can be in conjunction with an anti-inflammatory agent.

The introducing of the immature dendritic cells and/or CTLs can be in conjunction with an adjuvant. The immature dendritic cells and/or CTLs and adjuvant can be combined to form a composition and the composition can be introduced intratumorally and/or through vessel into the patient. The adjuvant can be selected from the group consisting of lipid-based, protein-based and polysaccharides-based adjuvants, such as lymphocyte cultured medium, Marignase, Agaricus, OK432, BCG, Lentinan (shiitake), Reishi, Sarunokoshikake, TNF Meshimakobu, Froint's complete or incomplete adjuvant, LPS, fatty acids, TW80, phospholipids, cytokines or a virus, and mixtures thereof. In certain embodiments, the adjuvant can be a leukocyte cultured medium (LCM) adjuvant. The LCM adjuvant can include at least three cytokines selected from the group consisting of eotaxin, FGF, G-CSF, GM-CSF, IFNγ, IP10, IL1β, IL1ra, IL2, IL4, IL5, IL6, IL7, IL8, IL9, IL10, IL12, IL13, IL15, IL17, MCP1, MIP1α, MIP1β, PDGFbb, RANTES, TNFα and VEGF.

In another aspect, the invention provides a method of regressing, reducing or eliminating tumor cells in a patient, which includes obtaining monocyte cells from the patient by isolating the monocyte cells from peripheral blood mononuclear cells, differentiating the monocyte cells to produce immature dendritic cells, combining a first sample of the immature dendritic cells with adjuvant and keyhole limpet to form a first mixture of the immature dendritic cells, introducing intratumorally and/or through vessel the first mixture of the immature dendritic cells into the patient, preparing CTLs from the monocyte-depleted peripheral blood mononuclear cells, introducing intratumorally and/or through vessel a first sample of the CTLs into the patient subsequent to introducing the first mixture of immature dendritic cells, combining a second sample of the immature dendritic cells with adjuvant to form a second mixture of the immature dendritic cells, introducing intratumorally and/or through vessel the second mixture of the immature dendritic cells to the patient, and introducing intratumorally and/or through vessel a second sample of the CTLs to the patient subsequent to introducing the second mixture of the immature dendritic cells.

BRIEF DESCRIPTION OF THE DRAWINGS

A further understanding of the invention can be gained from the following description of the preferred embodiments when read in conjunction with the accompanying drawings in which.

DETAILED DESCRIPTION OF PREFERRED EMBODIMENTS

Figure 1:
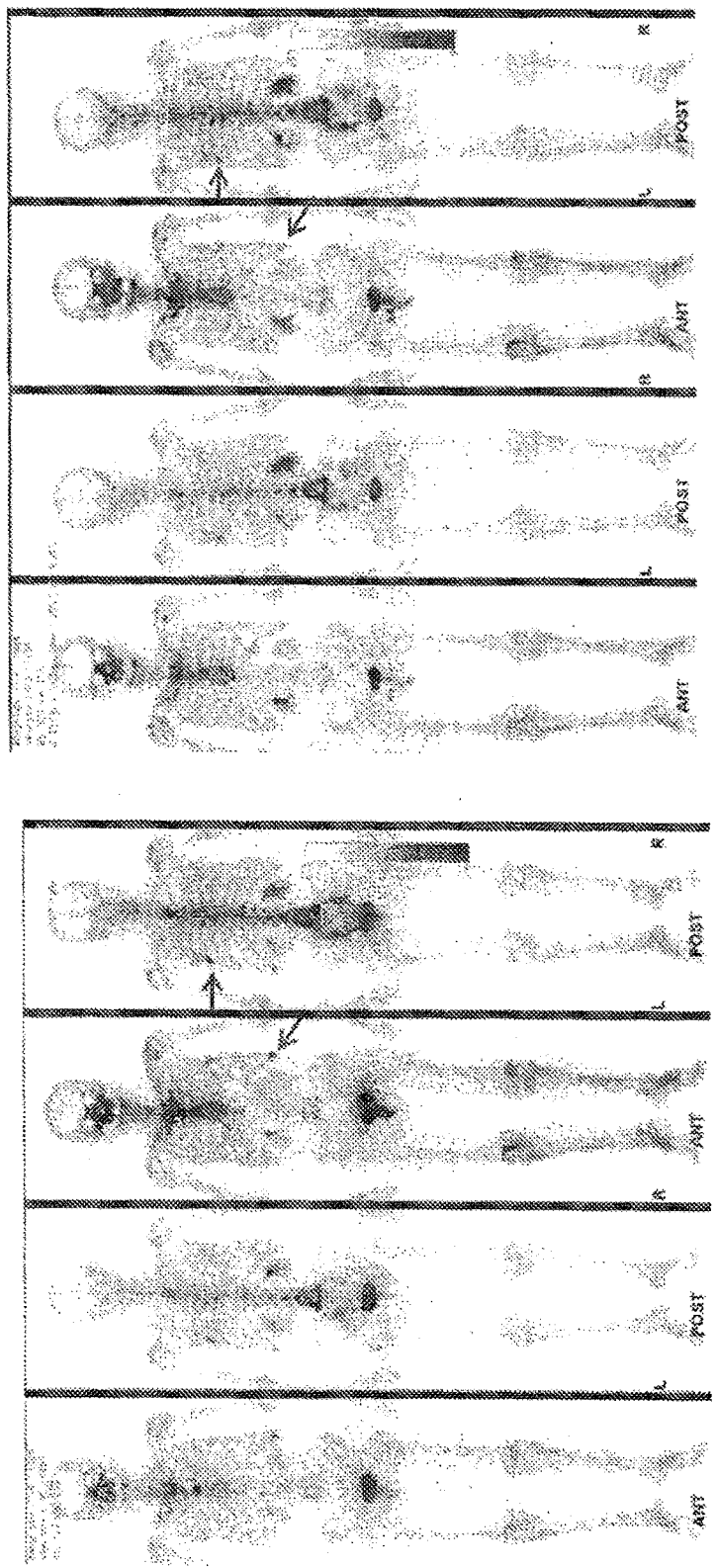
FIG. 1 is a radioisotope image of lt. ribs 7 and 10 showing tumor tissue before and after therapy, in accordance with one embodiment of this invention.

The invention includes introducing into a patient immature dendritic cells and/or cytotoxic T lymphocytes (CTLs) and anti-tumor necrosis factor (anti-TNF) antibody. The immature dendritic cells and/or CTLs are introduced to the patient intratumorally and/or through vessel, and the anti-TNF antibody is introduced to the patient intratumorally and/or through vessel and/or subcutaneously. The time between introducing the immature dendritic cells and/or CTLs and introducing the anti-TNF antibody can vary. The time period may range from zero (they are introduced simultaneously) to several seconds to several minutes to several hours to several days. In certain embodiments, the anti-TNF antibody is introduced coincident with introduction of the immature dendritic cells and/or CTLs. In other embodiments, the anti-TNF antibody is introduced immediately following or a short time thereafter the introduction of the immature dendritic cells and/or CTLs. In general, the anti-TNF antibody is introduced when there is a sufficient amount of CTLs present in the auto-immune system of the patient, such that the immune response of the CTLs is supported by suppressing the activity of the TNF.

Further, the time between introducing the immature dendritic cells and the CTLs can vary. The time period may range from zero (they are introduced simultaneously) to several seconds to several minutes to several hours to several days. In certain embodiments, the CTLs are introduced coincident with introduction of the immature dendritic cells. In other embodiments, the CTLs are introduced immediately following or a short time thereafter the introduction of the immature dendritic cells.

The therapy and methods of the invention are effective to induce regression, reduction or elimination of tumor cells, tumor tissue, and one or more tumors including tumors formed by metastasis. Further, this regression, reduction or elimination can be achieved in the presence or in the absence of conventional therapy, such as, but not limited to, radiotherapy and chemotherapy. In certain embodiments, therapy and methods of the invention is administered to a patient without additionally subjecting the patient to radiotherapy and/or chemotherapy.

As used herein, "patient(s)" include mammal(s), which include human(s).

As used herein, the term "therapeutically effective amount" refers to that amount of CTLs, anti-TNF antibody, immature dendritic cells, anti-inflammatory agent, adjuvant, or combinations thereof, required to bring about a desired effect in a human or other mammal. In all instances, at its most basic level, the desired effect is a regression, reduction or elimination of tumor cells in tumor tissue of the patient when compared to the tumor cells in the tumor tissue of the patient prior to employing the therapy and methods of the invention.

As used herein, the term "subcutaneous" and related terms employing "subcutaneous" or "subcutaneously" refer to therapy that includes the introduction of anti-TNF antibody beneath the skin of a patient, e.g., hypodermic.

As used herein, the term "through vessel" and related terms employing "through vessel" refer to therapy that includes the introduction of immature dendritic cells and/or CTLs and/or anti-TNF antibody into a channel, such as, a vein or artery, in a patient's body for carrying fluid.

As used herein, the term "intratumoral therapy" and related terms employing "intratumoral" or "intratumorally" refer to therapy that includes the introduction (e.g., injection) of immature dendritic cells and/or CTLs and/or anti-TNF antibody directly into the tumor tissue of a patient.

The anti-TNF antibody can be in various forms known in the art. The anti-TNF antibody can be incorporated into a delivery mechanism, such as a carrier or medium, to facilitate introduction into the patient. In certain embodiments, the anti-TNF antibody can be included or contained in a liquid for ease of introduction, e.g., injection.

It is known that TNF circulates throughout the body of a patient, contributes to effective immune surveillance, and is required for proper proliferation and function of natural killer cells, T cells, e.g., CTLs, B cells, macrophages, and dendritic cells, as well as, the regulation of immune cells. Further, it is known that the presence of TNF can cause systemic inflammation.

In accordance with the invention, it has been found that the introduction of immature dendritic cells in a patient can positively promote an immunoresponse to induce CTLs. In addition, introduction of the immature dendritic cells can induce the TNF level in the patient's bloodstream and increase inflammation at the tumor site(s), which can interfere with or hinder the immunoresponse of the CTLs and, in turn, induce inflammation at the tumor site, and progress the growth of the tumor. Thus, anti-TNF antibody can be combined (e.g., co-introduced or co-injected) with the CTLs to inhibit the induced inflammation.

In the therapy and methods of the invention, introduction of anti-TNF antibody intratumorally and/or through vessel and/or subcutaneously is effective to suppress the systemic inflammation caused by TNF. By suppressing this inflammation, the CTLs. e.g., induced by the introduction of the immature dendritic cells and/or CTLs, are not limited in their immunological function and therefore, are effective to destroy tumor cells both locally and systemically in the patient. The result of this immunological function can vary and may depend on the amount of tumor cells, CTLs and TNF in the patient's body. In certain embodiments, these factors are used to determine a therapeutically effective amount of anti-TNF antibody to be introduced or administered to the patient in order to achieve a favorable outcome, e.g., to maximize the regression, reduction or elimination of tumor cells (local and metastasized) in the patient. It is contemplated that an appropriate balance of the amount of tumor cells and TNF present in the patient's body, the amount of CTLs induced by the introduction intratumorally and/or through vessel of immature dendritic cells and/or CTLs, and the amount of anti-TNF antibody intratumorally and/or through vessel and/or subcutaneously introduced into the patient's body results in maximizing the effect of the therapy and the regression of tumors.

Further, even though it is known that the regulatory T-cell is a suppressing factor against local and/or systemic immunological response, it is found that the therapy and methods of the invention which control, e.g., suppress, the TNF-based inflammation (instead of the regulatory T-cell) are effective to treat tumors. In certain embodiments, the therapy and methods of the invention are particularly effective to treat multiple metastasized tumors.

Further, without intending to be bound by any particular theory, it is believed that CTLs, which are naturally induced as part of the autoimmune response above-described, may not be potent against tumors especially when the tumors are at an advanced stage or aggressively growing. The reasons may be that these CTLs are not induced in an adequate quality and/or in an adequate quantity and/or in a timely manner to defend the patient's body from the tumor invasion.

Since CTLs are produced by the patient, in certain embodiments, CTLs can be collected from the patient, cultured, and then introduced, e.g., returned, to the same patient's body. The culture medium can vary and may be selected from those known in the art. Non-limiting examples include, but are not limited to, IL-2, CD3, and mixtures thereof.

In certain embodiments, the invention includes collecting monocyte cells from the patient. The monocyte cells are cultured to form immature dendritic cells which are then introduced, e.g., returned, to the same patient's body. The culture medium can vary and may be selected from those known in the art. Non-limiting examples include, but are not limited to, IL-4, GM-CFS, and mixtures thereof.

In certain embodiments, the CTLs are collected from the patient following collection, culture and return of the immature dendritic cells into the patient. Subsequent to their collection, the CTLs are cultured in a suitable medium and then introduced, e.g., returned, to the same patient's body.

The immature dendritic cells and/or CTLs are introduced intratumorally and/or through vessel into the patient. In alternative embodiments, only immature dendritic cells are introduced or only CTLs are introduced or a combination of immature dendritic cells and CTLs are introduced into the patient. The CTLs can be introduced prior to, coincident with or following the intratumoral and/or through vessel introduction of the immature dendritic cells.

The anti-TNF can be introduced intratumorally and/or thorough vessel and/or subcutaneously into the patient in a therapeutically effective amount prior to, coincident with, or following introducing the cultured CTLs and/or immature dendritic cells.

In accordance with the invention, an adequate quantity and quality of CTLs are provided in the patient's body and, in particular, at the tumor site(s), to regress, reduce or eliminate tumor cells. Further, the CTLs are combined with anti-TNF to inhibit potential inflammation at the tumor site(s). It is contemplated that the quantity and quality of the natural CTLs (i.e., induced by the introduction of immature dendritic cells into the patient) may be sufficient (e.g., a therapeutically effective amount) to accomplish this objective. However, it is also contemplated that the quantity and quality of the natural CTLs may be insufficient and therefore, the invention provides for collecting the natural CTLs from the patient, culturing or activating these collected cells, and re-introducing them, e.g., in combination with anti-TNF, into the same patient in a quantity and quality which is sufficient (e.g., a therapeutically effective amount) to regress, reduce or eliminate tumor cells and to inhibit inflammation at the tumor site(s).

In general, the anti-TNF antibody is introduced when there is a sufficient amount of CTLs presenting in the autoimmune system of the patient, such that the immune response of the CTLs is supported by suppressing the activity of the TNF.

In certain embodiments, the CTLs include CD8+NK T cell population.

In certain embodiments, the invention is a human-initiated therapeutic vaccine with immature dendritic cells and/or CTLs in combination with anti-TNF antibody.

In certain embodiments, the immature dendritic cells and/or CTLs are introduced in conjunction with an adjuvant. The adjuvant can be introduced intratumorally and/or through vessel into the patient prior to, coincident with or following intratumoral and/or through vessel introduction of the immature dendritic cells and/or CTLs. In certain embodiments, the immature dendritic cells and/or CTLs and the adjuvant can be combined to form a composition and the composition can be introduced intratumorally and/or through vessel into the patient. Further, the immature dendritic cells and/or CTLs, and optionally adjuvant, are introduced intratumorally and/or through vessel prior to, coincident with or following introducing intratumorally and/or through vessel and/or subcutaneously anti-TNF antibody into the patient.

Suitable adjuvants for use in the invention can include, without limitation, lipid-based, protein-based and polysaccharides-based adjuvants, such as lymphocyte cultured medium, Marignase, Agaricus, OK432, BCG, Lentinan (shiitake), Reishi, Sarunokoshikake, TNF Meshimakobu, Froint's complete or incomplete adjuvant, LPS, fatty acids, TW80, phospholipids, cytokines or a virus. In certain embodiments, the adjuvant can be a leukocyte cultured medium (LCM) adjuvant. The LCM adjuvant can include at least three cytokines selected from the group consisting of eotaxin, FGF, G-CSF, GM-CSF, IFNγ, IP10, IL1β, IL1ra, IL2, IL4, IL5, IL6, IL7, IL8, IL9, IL10, IL12, IL13, IL15, IL17, MCP1, MIP1α, MIP1β, PDGFbb, RANTES, TNFα and VEGF.

In certain embodiments, the immature dendritic cells and/or CTLs can be introduced to the patient in conjunction with an anti-inflammatory agent. Suitable anti-inflammatory agents can include those that are known in the art. The anti-inflammatory agent can be introduced prior to, coincident with or following introduction of the immature dendritic cells and/or CTLs. It is typical for introduction of the immature dendritic cells, CTLs and anti-inflammatory agent to be simultaneous or substantially simultaneous, or for the elapsed time between introducing the immature dendritic cells and/or CTL and the anti-inflammatory agent to be relatively short in duration.

The invention can optionally include a precursor treatment. That is, prior to introducing the dendritic cells and/or CTLs, the patient may be administered a treatment selected from chemotherapy, radiotherapy, antibody therapy, and combinations thereof. These regimens are well known in the art. Further, optionally, it is contemplated that the use of these regimens may be employed at various other times throughout the method of the invention. However, it is further understood, that these regimens are not necessary. The therapy and methods of the invention are effective to regress, reduce or eliminate tumor tissue in a patient in the absence of chemotherapy, radiotherapy, antibody therapy, and combinations thereof.

The method of administering the therapy according to certain embodiments of the invention includes the following steps.

Step 1: Collecting monocyte cells and/or CTLs from a patient. Various conventional techniques known in the art can be employed for their collection.

Step 2: Culturing the monocyte cells and/or culturing/activating the CTLs collected from the patient. The monocyte cells form immature dendritic cells. Various conventional techniques known in the art can be employed to culture the monocyte cells and/or to culture/activate the CTLs, and various culture mediums known in the art can be used, such as those disclosed herein.

Step 3: Introducing intratumorally and/or through vessel, such as but not limited to injecting, a therapeutically effective amount of the immature dendritic cells and/or CTLs into the patient. The immature dendritic cells and/or CTLs can be mixed or combined with an adjuvant and the mixture or combination can be introduced intratumorally and/or through vessel into the patient. The adjuvant can be selected from those known in the art and disclosed herein. Further, optionally, an anti-inflammatory agent may be present with the immature dendritic cells and/or CTLs and adjuvant as disclosed herein.

Step 4: Introducing intratumorally and/or through vessel and/or subcutaneously, such as, but not limited to, injecting, a therapeutically effective amount of anti-TNF antibody into the patient. In certain embodiments, the anti-TNF antibody can be mixed or combined with anti-IL-10 and this mixture or combination can be introduced intratumorally and/or through vessel and/or subcutaneously into the patient.

The anti-TNF antibody can be introduced coincident with or immediately following or a short time after the introduction of the immature dendritic cells and/or CTLs into the patient.

The time allowed to lapse between and within the above-identified steps can vary. For example, the time allowed to lapse between Steps 3 and 4 can vary. In certain embodiments, Step 3 can be performed coincident with Step 4 and in other alternate embodiments, Step 4 can be performed following Step 3, such as a couple of seconds, hours, days, or weeks after Step 3.

The time allowed to lapse within Step 3, i.e., between the introduction of the immature dendritic cells and CTLs, can also vary. In certain embodiments, their introduction is simultaneous or substantially simultaneous. In other embodiments, there is a pre-determined or desired time period which is allowed to lapse between the introduction of each. It is typical for this period of time to be relatively short in duration.

Further, as previously indicated, the CTLs can be collected from the patient coincident with collection of the monocyte cells or at a time thereafter. In certain embodiments, the monocyte cells are collected and cultured to form immature dendritic cells and the dendritic cells are introduced into the patient prior to collection of CTLs from the patient.

Furthermore, as previously indicated, conventional therapy, such as, radiation or chemotherapy, may be conducted at any time during Steps 1 through 4.

In certain embodiments, the invention can include the treatment steps of: introducing intratumorally and/or through vessel immature dendritic cells in a therapeutically effective amount into the tumor tissue of the patient; collecting from the patient CTLs induced by the introduction of the immature dendritic cells; re-introducing intratumorally and/or through vessel the collected cytotoxic T lymphocyte into the tumor tissue of the same patient; and introducing intratumorally and/or through vessel and/or subcutaneously anti-TNF and/or anti-IL-10 into the patient. The introduction of the immature dendritic cells is a prerequisite to the collection and introduction of the CTLs cells with the anti-TNF and/or anti-IL-10 for inducement of the natural CTLs.

In certain embodiments, the inducement of CTLs by the immature dendritic cells is sufficient (e.g., a therapeutically effective amount) such that the natural CTLs are not removed from the patient and not re-introduced into the same patient. Thus, the anti-TNF and/or anti-IL-10 can be introduced to inhibit inflammation in the absence of the introduction of CTLs. That is, the introduction of immature dendritic cells can be in combination with the introduction of the anti-TNF and/or anti-IL-10.

Without intending to be bound by any particular theory, it is believed that immature dendritic cells which are formed by culturing monocyte cells collected from a patient and CTLs which are produced by a patient and collected from the patient, provide for an enhanced desired effect when injected into the same patient as compared to immature dendritic cells and CTLs produced and obtained by other means. It appears that immature dendritic cells which are formed from the patient's own monocyte cells which have been collected and CTLs which have been collected, cultured and re-introduced intratumorally and/or through vessel, provide improved coupling or interaction with other cells in the body of the patient.

In certain embodiments, the invention provides regression, reduction or elimination of tumor cells in tumor tissue which can be visually detected by MRI and/or CT and/or Echo scan.

Further, in certain embodiments of the invention, a combination of immunotherapy and local radiation is administered to a cancer patient. Without intending to be bound by any particular theory, it is believed that this combination of treatments provides for a therapeutic protocol to stimulate a systemic adaptive immune response against malignant cells. In accordance with this protocol, monocyte cells are obtained from the patient for differentiation into immature dendritic cells. The monocyte cells are isolated from peripheral blood mononuclear cells (PBMCs). The monocyte cell-depleted. T-cell enriched fraction of the PBMCs is then used to prepare activated T-cells, e.g., CTLs. The immature dendritic cells are combined with LCM, a multi-cytokine-based adjuvant, and keyhole limpet hemocycanin (KLH). This mixture is injected into the patient. Subsequently, such as but not limited to, on the following day, activated T-cells, e.g., CTLs, are infused. After a period of time, such as, but not limited to, about seven days, local radiation is administered to the patient. After a period of time, such as, but not limited to, about another seven days, a second sample of immature dendritic cells and activated T-cells, e.g., CTLs, is administered to the patient. For example, immature dendritic cells suspended in LCM are injected and then, e.g., on the following day, activated T-cells, e.g., CTLs, are infused. It has been found that this protocol results in an increase in $CD8^+$ $CD56^+$ cells. Without intending to be bound by any particular theory, it is believed that these cells are capable of killing cancer cells.

EXAMPLES

Example 1

A MRI was performed on a 71 year-old male patient and the patient was diagnosed with Stage IV prostatic cancer and multiple bone metastasis. The patient had advanced cancer and progressive disease that had not responded to conventional standard therapies. Apheresis was performed on the patient to collect moncyte cells from the patient. The monocyte cells were cultured with IL4 and GM-CFS. This resulted in the production of immature dendritic cells. A cocktail was prepared containing between about $10^7$ to $10^8$ immature dendritic cells and between about 1.0 to 2.0 mg of LCMadj to make up a 10% concentration in normal saline. Depending on the size of the tumor, between 2.0 and 5.0 cc of normal saline was injected into multiple tumor sites of the patient. The patient was also administered radiotherapy and a subsequent intratumoral injection of the cocktail containing the immature dendritic cells and LCMadj.

Apheresis was performed on the patient to collect CTLs from the patient. The CTLs were cultured and a cocktail was prepared containing from $10 \times 10^8$ to $30 \times 10^8$ of the cultured CTLs and 12.5 mg to 50.0 mg of anti-TNF. The cocktail was injected into multiple tumor sites of the patient. The detailed protocol is shown in Table 1.

The patient was evaluated by RI image analysis. Four of the treated tumors of the patient showed complete response (CR), two of the treated tumors showed partial response (PR) and all of the other treated sites showed stable disease (SD). CR is defined as a decrease in serum markers to normal levels and complete disappearance of all measurable lesions. PR is defined as a 30% reduction in the size of the injected tumor, a decline in serum markers, no increase in tumor size at other metastatic sites or appearance of new metastasis. SD is defined as showing less than a 20% increase in tumor size and less than a 30% reduction in tumor size, with no increase in serum tumor markers.

FIG. 1 shows before (e.g., prior to the injection of the CTL and anti-TNF cocktail as described above) and after (e.g., following the injection of the CTL and anti-TNF cocktail as described above) RI images of the lt. rib 7 and 10. These treated tumors were two of the four treated tumors of the patient that showed complete response.

Example 2

A 74 year-old male patient was diagnosed with Stage III prostatic cancer and multiple bone metastasis. The patient had advanced cancer and progressive disease that had not responded to conventional standard therapies. Apheresis was performed on the patient to collect moncyte cells from the patient. The monocyte cells were cultured with IL4 and GM-CFS. This resulted in the production of immature dendritic cells. A cocktail was prepared containing between about $10^7$ to $10^8$ immature dendritic cells and between about 1.0 to 2.0 mg of LCMadj to make up a 10% concentration in normal saline. Depending on the size of the tumor, between 2.0 and 5.0 cc of normal saline was injected into multiple tumor sites of the patient. The patient was also administered radiotherapy and a subsequent intratumoral injection of the cocktail containing the immature dendritic cells and LCMadj.

Apheresis was performed on the patient to collect CTLs from the patient. The CTLs were cultured and a cocktail was prepared containing $30 \times 10^8$ of the cultured CTLs and 37.5 mg of anti-TNF. The cocktail was injected into multiple tumor sites of the patient, including sacrum, Th7, Th10, Th12, L1, L3, Rt. ilium, Lt. ilium, Lt. rib 6(1)(2), Lt. rib 10, and Rt. femur. The detailed protocol is shown in Table 2.

The patient was evaluated by RI image analysis. Three of the treated tumors of the patient showed PR (as defined above) and the remaining treated tumors showed CR (as defined above).

Figure 2:
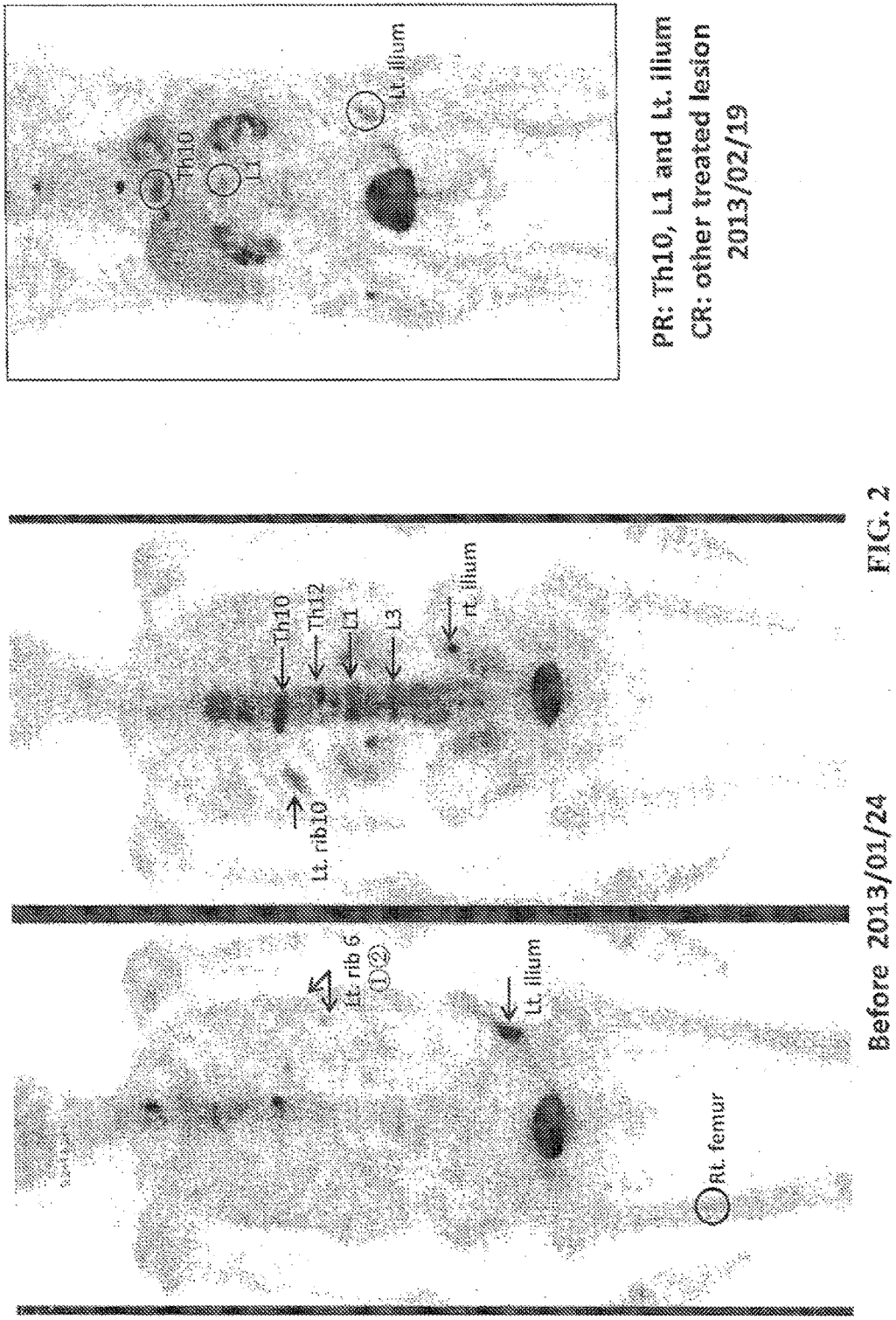
FIG. 2 is a radioisotope image of Th10, L1, lt. ilium, lt. rib 6, Rt. femur, lt. rib 10, Th12, L3 and rt. ilium showing tumor tissue before and after therapy, in accordance with one embodiment of this invention.

FIG. 2 shows before (e.g., prior to the injection of the CTL and anti-TNF cocktail as described above) and after (e.g., following the injection of the CTL and anti-TNF cocktail as described above) RI images of the Th10, L1 and Lt. ilium. These treated tumors were the three treated tumors of the patient that showed PR. Further, FIG. 2 shows before RI images of the Lt. rib 6, Rt. femur, Lt. rib 10, Th12, L3 and Rt. ilium. These are the treated tumors that showed CR.

Example 3

A 51 year-old female patient was diagnosed with Stage IV breast cancer and Lt. axilla LN metastasis. The patient had advanced cancer and progressive disease that had not responded to conventional standard therapies. Apheresis was performed on the patient to collect moncyte cells from the patient. The monocyte cells were cultured with IL4 and GM-CFS. This resulted in the production of immature dendritic cells. A cocktail was prepared containing between about $10^7$ to $10^8$ immature dendritic cells and between about 1.0 to 2.0 mg of LCMadj to make up a 10% concentration in normal saline. Depending on the size of the tumor, between 2.0 and 5.0 cc of normal saline was injected into multiple tumor sites of the patient. The patient was also administered radiotherapy and, subsequent intratumoral injections of immature dendritic cells and LCMadj in combination with 25.0 mg of anti-TNF. The detailed protocol is shown in Table 3.

The patient was evaluated by RI image analysis. The treated tumors of the patient showed PR and CR.

Figure 3:
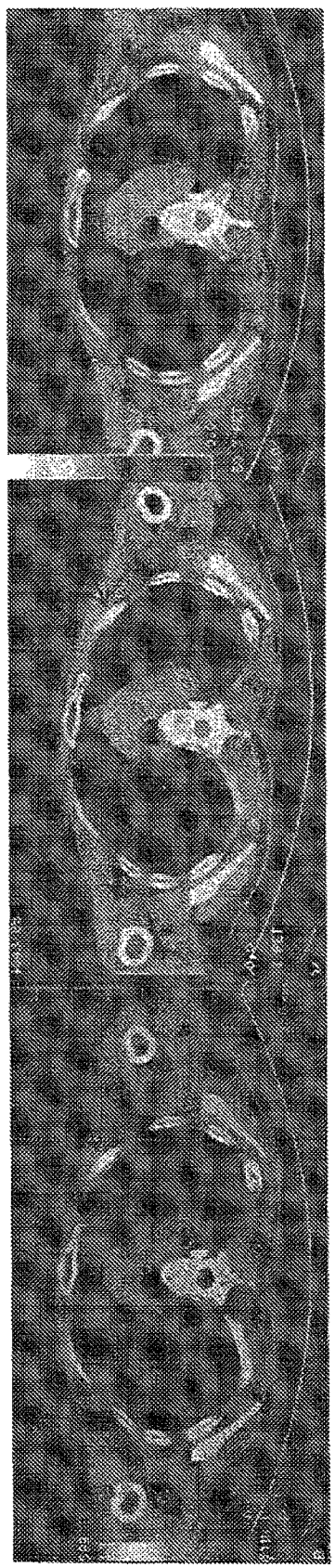
FIG. 3 is a radioisotope image of lt. rib 2 showing tumor tissue before and after therapy, in accordance with one embodiment of this invention.

FIG. 3 shows before and after (PR and CR) RI images of the lt. rib 2.

Example 4

A 79 year-old female patient was diagnosed with Stage II lung cancer and brain metastasis. The patient had advanced cancer and progressive disease that had not responded to conventional standard therapies. Apheresis was performed on the patient to collect moncyte cells from the patient. The monocyte cells were cultured with IL4 and GM-CFS. This resulted in the production of immature dendritic cells. A cocktail was prepared containing between about $10^7$ to $10^8$ immature dendritic cells and between about 1.0 to 2.0 mg of LCMadj to make up a 10% concentration in normal saline. Depending on the size of the tumor, between 2.0 and 5.0 cc of normal saline was injected into multiple tumor sites of the patient. The patient was also administered radiotherapy and a subsequent intratumoral injection of the cocktail containing the immature dendritic cells and LCMadj.

Apheresis was performed on the patient to collect CTLs from the patient. The CTLs were cultured and a cocktail was prepared containing from $10 \times 10^8$ to $40 \times 10^8$ of the cultured CTLs and 12.5 mg to 25.0 mg of anti-TNF. The cocktail was injected into multiple tumor sites of the patient. The detailed protocol is shown in Table 4.

The patient was evaluated by RI image analysis. The treated tumors of the patient showed CR.

Figure 4:
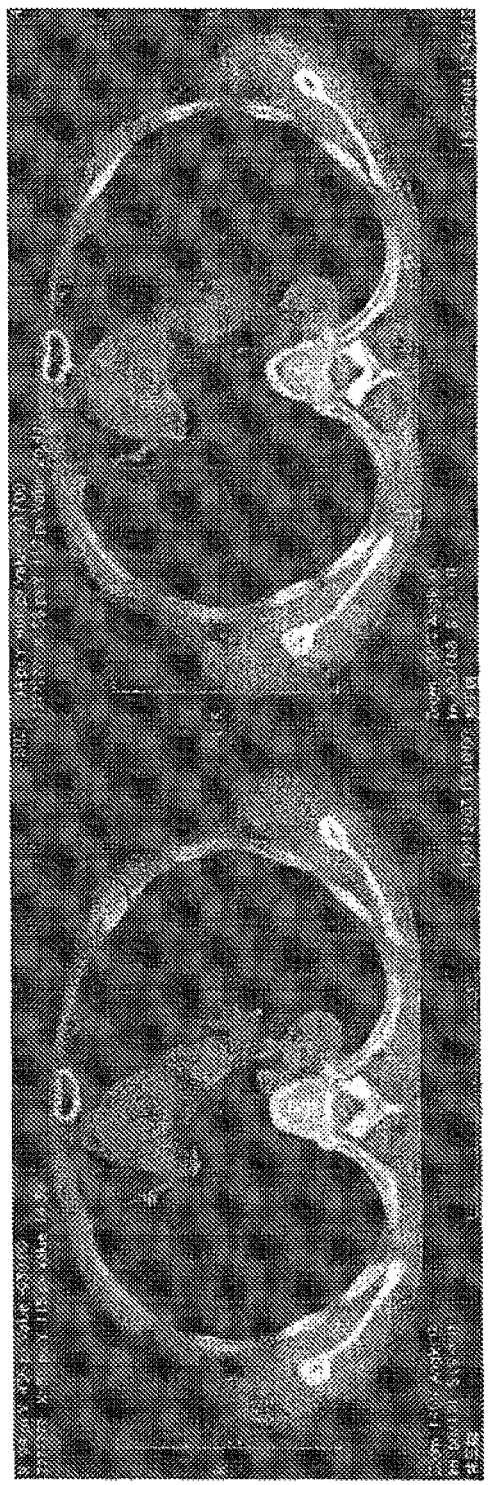
FIG. 4 is a radioisotope image of lt. rib 3 showing tumor tissue before and after therapy, in accordance with one embodiment of this invention.

FIG. 4 shows before and after RI images of the lt. rib 3. This treated tumor showed complete response.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

TABLE 1

Protocol HITV & CTL-II (intra-tumoral)
Prostatic Cancer (Stage IV), Multiple Bone Metastasis
(#0442, 71Y Male)

| Date | Event |
|---|---|
| 2007 February | MRI found prostatic cancer, bone metastasis Endocrine therapy: leuplin/casodex |
| 2007 September | MRI: CR (pancreas), PR (bone meta.) |
| 2008 November | Rec. |
| 2009 September | Peptide DC, vitamin C and ozone therapy |
| 2010 January | MRI: Difuse meta. to the pelvis |
| 2010 February | IMRT to the prostate gland + pelvis meta. |
| 2010 March | MRI: mult. bone meta. |
| 2010 Mar. 25 | IMRT: 48.3Gy/20F/21D (primary, SV, bil inguinal LN) 56.2Gy/20F/21D (other bone meta.) |
| 2010 Apr. 4 | Apheresis |
| 2010 Apr. 29 | DC injection to 20 sites |
| 2010 Jun. 1 | DC injection to 30 sites |
| 2010 Jun. 7 | IMRT: 40.0Gy/10Fr/12D |
| 2010 Aug. 6 | MRI: CR (prostate gland) PR (thoracic spine) Rec. (multiple bone) |
| 2010 Oct. 26 | RI: Rec. (multiple bone) |
| 2010 Nov. 15 | IMRT: 26.26Gy/12F/19D (mult. bone meta.) |
| 2010 Dec. 1 | IMRT: 30.00Gy/5Fr/9D (rt. ischium, bil. femur) |
| 2010 Dec. 15 | DC injection to 21 sites |

TABLE 1-continued

Protocol HITV & CTL-II (intra-tumoral)
Prostatic Cancer (Stage IV), Multiple Bone Metastasis
(#0442, 71Y Male)

| Date | Event |
|---|---|
| 2011 Apr. 21 | RI: PR (lumbar~pelvis) PD (cervical~thoracic) |
| 2011 Jul. 22 | RI: SD (bone meta. overall) |
| 2011 Dec. 9 | CTL apheresis |
| 2011 Dec. 9 | CTL (25.0 × 10*8) w/anti-TNF 25.0 mg (L4/L5) |
| 2012 Jan. 13 | CTL (25.0 × 10*8) w/anti-TNF 25.0 mg (L3/lt.ilium) |
| 2012 Feb. 3 | RI: CR (L4/L3) PR (L5/lt. ilium) Untreated residual tumor (lt. rib 7&10, sternum) |
| 2012 Mar. 28 | CTL (20.0 × 10*8) w/anti-TNF 25.0 mg (lt. rib7&10, sternum) |
| 2012 May 11 | RI: PR (Lt. rib 7&10) SD (sternum) |
| 2012 May 17 | CTL apheresis |
| 2012 Jun. 21 | CTL (10.0 × 10*8) w/anti-TNF 12.5 mg (lt. rib7) |
| 2012 Jul. 19 | CTL apheresis |
| 2012 Aug. 9 | CTL (10.0 × 10*8) w/anti-TNF 12.5 mg (lt.rib10) |
| 2012 Aug. 10 | RI: CR (Lt. rib 10 SD (Lt. rib 7) Rec. (rt. sacrum) |
| 2012 Sep. 3 | CTL (30.0 × 10*8) w/anti-TNF 37.5 mg (stenum/rt.sacrum/lt. ilium) |
| 2012 Oct. 4 | CTL (30.0 × 10*8) w/anti-TNF 37.5 mg (Th7/Th8/Lt.rib7) |
| 2012 Nov. 5 | Apheresis |
| 2012 Nov. 5 | CTL (20.0 × 10*8) w/anti-TNF 50.0 mg (Lt.5/Rt.L5/Th3/Th4) |
| 2012 Nov. 19 | RI: CR (Lt. rib 7) SD (other treated sites) |
| 2012 Dec. 3 | DC w/anti-TNF 50.0 mg to each site (Rt. rib1/sternum) |
| 2013 Jan. 8 | DC w/anti-TNF 50.0 mg to each site (Th3) |
| 2013 Feb. 5 | DC w/anti-TNF 50.0 mg to each site (Lt.L5/Rt.L5) |

TABLE 2

Protocol HITV & CTL-II (intra-tumoral)
Prostatic Cancer (Rec.), Multiple Bone Metastasis
(#0611, 74Y Male)

| Date | Event |
|---|---|
| 2006 May | Prostatic cancer (stage III) Brachytherapy |
| 2011 May 12 | Bone scintigram found many bone meta. |
| 2011 May 23 | Apheresis |
| 2011 Jun. 3 | DC injection to 15 bone meta. |
| 2011 Jun. 8 | IMRT: 48.5Gy/10F/14D |
| 2011 Jun. 24 | DC injection |
| 2011 Jul. 22 | Apheresis |
| 2011 Aug. 5 | RI: PR (all treated sites) |
| 2011 Sep. 9 | Weekly CTL div. started |
| 2012 Apr. 16 | RI: SD~PR overall, new lesion at sacrum & th8 |
| 2012 May 30 | Apheresis |
| 2012 May 30 | CTL (30.0 × 10^8) w/anti-TNF 37.5 mg to th7, lt. ilium, sacrum |
| 2013 Jan. 24 | RI: many bone meta. up |
| 2013 Feb. 8 | DC w/anti-TNF 25.0 mg to each site: th10, th12, L1, L3, rt. ilium, lt. ilium, lt. rib 6 ① ②, lt. rib 10, and rt. femur |
| 2013 Feb. 19 | PET-CT: PR~CR, new lesion C4 |

TABLE 3

Protocol HITV & CTL-II (intra-tumoral)
Breast Cancer (Stage IV), axilla LN metastasis
(#0675, 51Y Female)

| Date | Event |
|---|---|
| 2011 Oct. 5 | PET-CT: lt. breast FDG uptake (refused surgery) |
| 2011 Oct. 20 | Biopsy: Invasive ductal carcinoma |
| 2011 Oct. 27 | Apheresis |
| 2011 Dec. 1 | DCAT injection (6 times) |
| 2012 Jan. 7 | Lt. axilla LN up (refused surgery) |
| 2012 Jan. 19 | Apheresis |

TABLE 3-continued

Protocol HITV & CTL-II (intra-tumoral)
Breast Cancer (Stage IV), axilla LN metastasis
(#0675, 51Y Female)

| | |
|---|---|
| 2012 Jan. 27 | DC injection to lt. breast (4 sites) and lt. axilla LN (3 sites) |
| 2012 Feb. 6 | IMRT: 48.32Gy/20Fr/30D (lt. whole breast) 60.00 Gy/30Fr/30D (Primary + lt. axilla LN) |
| 2012 Mar. 9 | DC injection to lt. breast (2 sites) and lt. axilla LN (4 sites) |
| 2012 Apr. 20 | PET-CT: CR |
| 2012 Jul. 20 | PET-CT: CR |
| 2012 Oct. 27 | PET-CT: CR, but new lesion up (lt. rib 2) |
| 2012 Nov. 9 | DC injection to the lt. rib 2 w/anti-TNF 25.0 mg |
| 2012 Nov. 26 | DC injection w/anti-TNF 25.0 mg |
| 2012 Dec. 27 | PET-CT: PR |
| 2013 Feb. 14 | PET-CT: CR |

TABLE 4

Protocol HITV & CTL-II (intra-tumoral)
Lung Cancer (Stage II), brain metastasis
(#0701, 79Y Female)

| | |
|---|---|
| 2011 August | Tumor enlargement no surgery because of her weak condition |
| 2011 Dec. 8 | PET-CT: rt. lung primary S3, rt. rib 2, 3, rt. hilar LN |
| 2011 Dec. 28 | Apheresis |
| 2012 Jan. 16 | IMRT: 24.5Gy/5F/5D to primary S3 40.0Gy/5F/5D to ribs |
| 2012 Jan. 24 | DC injection to rt. primary (3 sites), rt. hilar LN, rt. rib 2 & 3 |
| 2012 Mar. 6 | PET-CT: PR (rt. primary), CR (rt. hilar and rt. ribs) New lesion: rt. lung S5, lt. lung S4 and lt. hilar LN |
| 2012 Mar. 14 | Apheresis |
| 2012 Apr. 26 | CTL (40.0 × 10*8) w/anti-TNF 12.5 mg (rt. primary S3, rt. chest cavity) |
| 2012 May 24 | CTL (10.0 × 10*8) w/anti-TNF 25.0 mg (lt. hilar LN) |
| 2012 Jun. 6 | PET-CT: PR (primary S3), CR (lt. hilar) and new lesion at lt. rib 6 |
| 2012 Jun. 13 | CTL (10.0 × 10*8) w/anti-TNF 25.0 mg (lt. rib 6) |
| 2012 Sep. 3 | PET-CT: PR (primary S3), CR (lt. rib 6,) no new lesion |
| 2012 Sep. 27 | CTL (10.0 × 10*8) w/anti-TNF 25.0 mg (rt. primary S3, rt. hilar LN) |
| 2012 Dec. 3 | PET-CT: both PR, new lesion at lt. rib 3 |
| 2013 Jan. 22 | DC injection w/anti-TNF 25.0 mg to lt. rib 3 |
| 2013 Mar. 4 | PET-CT: CR |

I claim:

1. A method of regressing, reducing or eliminating tumor cells in a patient comprising:
   obtaining monocyte cells from the patient;
   differentiating the monocyte cells to produce immature dendritic cells;
   combining the immature dendritic cells with adjuvant to form a mixture of the immature dendritic cells;
   introducing intratumorally and/or through vessel the mixture of the immature dendritic cells into the patient;
   obtaining CTLs from the patient;
   culturing the CTLs to produce cultured CTLs;
   introducing intratumorally and/or through vessel the cultured CTLs into the patient; and
   injecting intratumorally anti-TNF antibody into the patient.

2. The method of claim 1, wherein the introducing intratumorally and/or through vessel of the cultured CTLs, is coincident with the injecting intratumorally introducing of the anti-TNF antibody.

3. The method of claim 1, wherein the patient is a human.

4. The method of claim 1, wherein the introducing of the immature dendritic cells and/or the cultured CTLs is in conjunction with the adjuvant.

5. The method of claim 4, wherein the immature dendritic cells and/or the cultured CTLs and the adjuvant are combined to form a composition and the composition is introduced intratumorally and/or through vessel into the patient.

6. The method of claim 4, wherein the adjuvant is selected from the group consisting of lipid-based, protein-based and polysaccharides-based adjuvants, and mixtures thereof.

7. The method of claim 6, wherein the adjuvant is selected from the group consisting of lymphocyte cultured medium, Marignase, Agaricus, OK432, BCG, Lentinan (shiitake), Reishi, Sarunokoshikake, TNF Meshimakobu, Froint's complete or incomplete adjuvant, LPS, fatty acids, TW80, phospholipids, cytokines or a virus, and mixtures thereof.

8. The method of claim 6, wherein the adjuvant comprises a leukocyte cultured medium (LCM).

9. The method of claim 8, wherein the LCM comprises at least three cytokines selected from the group consisting of eotaxin, FGF, G-CSF, GM-CSF, IFNγ, IP10, IL1β, IL1ra, IL2, IL4, IL5, IL6, IL7, IL8, IL9, IL10, IL12, IL13, IL15, IL17, MCP1, MIP1α, MIP1β, PDGFbb, RANTES, TNFα and VEGF.

10. The method of claim 1, wherein the injecting intratumorally of the anti-TNF antibody is immediately following or a short time after the introducing intratumorally and/or through vessel of the immature dendritic cells and/or the cultured CTLs.

11. The method of claim 10 wherein a short time after can be in a range from a couple of seconds to a couple of minutes to a couple of hours to a couple of days.

12. The method of claim 1, further comprising culturing the monocyte cells in a culture medium selected from the group consisting of IL-4, GM-CFS, and mixtures thereof.

13. The method of claim 1, wherein the culturing of the CTLs is carried out in a culture medium selected from the group consisting of IL-2, CD3, and mixtures thereof.

14. The method of claim 1, wherein a therapeutically effective amount of the anti-TNF antibody is injected intratumorally and said therapeutically effective amount is dependent on an amount of tumor cells, TNF and CTLs present in the patient.

15. The method of claim 1, wherein the tumor cells are present in metastasized tumor tissue.

16. The method of claim 1, wherein the method is carried out in the absence absent of conventional therapy selected from the group consisting of chemotherapy, radiotherapy and combinations thereof.

17. The method of claim 1, further comprising introducing anti-IL-10, anti-IL-6 or mixtures thereof.

18. A method of regressing, reducing or eliminating tumor cells in a patient comprising:
   obtaining monocyte cells from the patient;
   differentiating the monocyte cells to produce immature dendritic cells;
   combining the immature dendritic cells with adjuvant to form a mixture of the immature dendritic cells;
   injecting intratumorally the mixture of the immature dendritic cells into the patient;
   obtaining CTLs from the patient;
   culturing the CTLs to produce cultured CTLs;
   injecting intratumorally the cultured CTLs into the patient; and
   injecting intratumorally anti-TNF antibody into the patient.

* * * * *